United States Patent [19]
Lin et al.

[11] 4,433,177
[45] * Feb. 21, 1984

[54] PROCESS FOR PREPARING ACETALDEHYDE FROM METHANOL AND SYNTHESIS GAS USING A NOVEL CATALYST COMPOSITION

[75] Inventors: Jiang-Jen Lin, Round Rock; John F. Knifton, Austin, both of Tex.

[73] Assignee: Texaco Inc., White Plains, N.Y.

[*] Notice: The portion of the term of this patent subsequent to Feb. 21, 2001 has been disclaimed.

[21] Appl. No.: 344,260

[22] Filed: Feb. 1, 1982

[51] Int. Cl.$^3$ .............................................. C07C 47/06
[52] U.S. Cl. ..................................... 568/487; 568/489; 568/496; 568/890; 568/902
[58] Field of Search ............... 568/489, 890, 902, 487, 568/496

[56] References Cited

U.S. PATENT DOCUMENTS 4,151,208 4/1979 Pretzer et al. ...................... 568/487
4,306,091 12/1981 Gauthier-Lafaye ................ 568/487
4,348,541 9/1982 Doyle ................................... 568/487

Primary Examiner—Werren B. Lone
Attorney, Agent, or Firm—Jack H. Park; Walter D. Hunter; Cynthia L. Kendrick

[57] ABSTRACT

Acetaldehyde is prepared from methanol and synthesis gas with good selectivity and yield by contacting a mixture of methanol, carbon monoxide and hydrogen with an iodide or iodine free catalyst composition comprising (1) ruthenium powder, (2) a cobalt-containing compound, (3) an amine, and (4) an onium salt or base, and heating the resulting mixture to an elevated temperature and pressure for sufficient time to produce the desired acetaldehyde, and recovering the same from the reaction mixture.

23 Claims, No Drawings

PROCESS FOR PREPARING ACETALDEHYDE FROM METHANOL AND SYNTHESIS GAS USING A NOVEL CATALYST COMPOSITION

BACKGROUND OF THE INVENTION

1. Field of the Invention

This invention relates to a new process for preparing acetaldehyde. More particularly, the invention relates to a new process for preparing acetaldehyde from methanol and synthesis gas using a novel catalyst composition.

Specifically, the invention provides a new and improved process for preparing acetaldehyde from methanol and syngas which gives good selectivity and improved yields, which process comprises contacting a mixture of methanol, carbon monoxide and hydrogen with an iodide or iodine-free catalyst composition comprising (1) ruthenium powder, (2) a cobalt containing compound, (3) an amine, and (4) an onium salt or base, and heating the resulting mixture to an elevated temperature and pressure for sufficient time to produce the acetaldehyde, and then recovering the same from the reaction mixture.

2. Prior Art

Acetaldehyde is an important chemical of commerce used in a great variety of applications, such as, for example, in the preparation of acetic acid, vinyl acetate, chloral, cyanohydrins and polyhydric alcohol derivatives, such as the glycol monoalkyl ethers. Acetaldehyde has been produced heretofore by methods, such as the hydration of acetylene or the oxidation of ethylene. Such methods, however, have their limitations, particularly as to cost, and it would be desirable to find a more economical method for producing this compound.

U.S. Pat. No. 4,151,208 discloses a method for producing acetaldehyde from methanol and syngas using a catalyst comprising a special cobalt compound and an iodine promoter. This process is limited, however, because of the serious corrosion problems due to the presence of the iodine promoter. U.S. Pat. No. 4,201,868 discloses a process for preparing a mixture of products containing acetaldehyde using a catalyst comprising a cobalt carbonyl and an organic nitrogen-containing ligand. This process, however, is limited by its poor selectivity.

It is an object of the invention, therefore, to provide a new and improved process for preparing acetaldehyde. It is a further object to provide a process for preparing acetaldehyde from methanol and syngas using a new and improved catalyst system. It is a further object to provide a new process for preparing acetaldehyde from methanol and syngas which gives very good selectivity and yield of the desired product. It is a further object to provide a process for preparing acetaldehyde which utilizes a catalyst system which is free of corrosive elements and is thus capable of use on a large commercial scale. These and other objects of the invention will be apparent from the following detailed description thereof.

SUMMARY OF THE INVENTION

It has now been discovered that these and other objects may be accomplished by the process of the invention comprising contacting methanol, carbon monoxide and hydrogen with an iodide and iodine-free catalyst composition comprising (1) ruthenium powder, (2) a cobalt-containing compound, (3) an amine, and (4) an onium salt or base, and heating the resulting mixture to an elevated temperature and pressure for sufficient time to produce the desired acetaldehyde, and recovering the same from the reaction mixture. It was surprising to find that this new catalyst system was highly selective for the conversion of methanol to the desired acetaldehyde in view of the discouraging results obtained with related catalyst systems. A further advantage of the process being that it avoids the use of catalysts containing corrosive elements, such as iodides or iodine-containing compounds, and is thus suited for use on a large commercial scale.

The high selectivity in the formation of the acetaldehyde obtained by the present process is particularly outstanding in view of the results obtained in a related process disclosed and claimed in our copending patent application Ser. No. 344,430 filed this same date, which does not employ the amine in the catalyst system. The improvement in the claimed process over that process is shown in the working examples at the end of the specification.

In order to present the inventive concept of the present invention in the greatest possible detail, the following supplementary disclosure is submitted. The process of the invention is practiced as follows:

As noted, the new catalyst system used in the process of the invention contains ruthenium metal powder, a cobalt-containing compound, an amine, and an onium salt or base. The ruthenium metal powder can be powdered ruthenium metal of any mesh size.

The cobalt-containing compound to be used in the catalyst composition may take many different forms. For instance, the cobalt may be added to the reaction mixture in the form of an oxide, salt, carbonyl derivative and the like. Examples of these include, among others, cobalt oxides $Co_2O_3$, $Co_3O_4$, CoO, cobalt(II) bromide, cobalt(II) thiocyanate, cobalt(II) phosphate, cobalt acetate, cobalt naphthenate, cobalt benzoate, cobalt valerate, cobalt cyclohexanoate, cobalt carbonyls, such as dicobalt octacarbonyl $Co_2(CO)_8$, tetracobalt dodecacarbonyl $Co_4(CO)_{12}$ and hexacobalt hexadecacarbonyl $Co_6(CO)_{16}$ and derivatives thereof by reaction with ligands and preferably group V donors, such as the phosphines, arsines and stilbines, such as $(Co(CO)_3L)_2$ wherein L is $PR_3$, $AsR_3$ and $SbR_3$ wherein R is a hydrocarbon radical, cobalt carbonyl hydrides, cobalt carbonyl bromide, cobalt nitrosyl carbonyls as $CoNO(CO)_3$, $Co(NO)(CO)_2PPh_3$, cobalt nitrosyl bromides, organometallic compounds obtained by reacting cobalt carbonyls with olefins, allyl and acetylene compounds, such as bis($\pi$-cyclopentadienyl) cobalt ($\pi C_5H_5)_2Co$, cyclopentadienyl cobalt dicarbonyl, bis(hexamethylenebenzene)cobalt.

Preferred cobalt-containing compounds to be used in the catalyst system comprise those having at least one cobalt atom attached to carbon, such as the cobalt carbonyls and their derivatives as, for example, dicobalt octacarbonyl, tetracobalt dodecacarbonyl, $(Co(CO)_3P(CH_3)_3)_2$, organometallic compounds obtained by reacting the cobalt carbonyls with olefins, cycloolefins, allyl and acetylene compounds such as cyclopentadienyl cobalt dicarbonyl, cobalt carbonyl bromides, cobalt carbonyl hydrides, cobalt nitrosyl carbonyls, and the like, and mixtures thereof.

Particularly preferred cobalt-containing compounds to be used in the catalyst comprise those having at least one cobalt atom attached to at least three separate carbon atoms, such as for example, the dicobalt octacarbonyls and their derivatives.

The quaternary onium salt or base to be used in the catalyst composition may be any onium salt or base, but are preferably those containing phosphorous or nitrogen, such as those of the formula

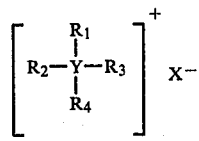

wherein Y is phosphorous or nitrogen, $R_1$, $R_2$, $R_3$ and $R_4$ are organic radicals preferably alkyl, aryl or alkaryl radicals, and X is an anionic species. The organic radicals useful in this instance include those alkyl radicals having from 1 to 20 carbon atoms in a branched or linear alkyl chain, such as methyl, ethyl, n-butyl, isobutyl, octyl, 2-ethylhexyl and dodecyl radicals. Tetraethylphosphonium bromide and tetrabutylphosphonium bromide are typical examples presently in commercial production. The corresponding quaternary phosphonium or ammonium acetates, hydroxides, nitrates, chromates, tetrafluoroborates and the corresponding chlorides are also satisfactory.

Equally useful are the phosphonium and ammonium salts containing phosphorous or nitrogen bonded to a mixture of alkyl, aryl and alkaryl radicals, which radicals preferably contain from 6 to 20 carbon atoms. The aryl radical is most commonly phenyl. The alkaryl group may comprise phenyl substituted with one or more $C_1$ to $C_{10}$ alkyl substituents, bonded to phosphorous or nitrogen through the aryl function.

Illustrative examples of suitable quaternary onium salts or bases include tetrabutylphosphonium bromide, n-heptyltriphenylphosphonium bromide, tetrabutylammonium chloride, tetrabutylphosphonium nitrate, tetrabutylphosphonium hydroxide, tetrabutylphosphonium chromate, tetraoctylphosphonium tetrafluoroborate, tetrahexyl phosphonium acetate and tetraoctylammonium bromide.

The preferred quaternary onium salts and bases to be used in the process comprise the tetralkylphosphonium salts containing alkyl groups having 1 to 6 carbon atoms, such as methyl, ethyl, butyl, hexyl, heptyl and isobutyl. Tetralkylphosphonium salts, such as the bromides and chlorides acetate and chromate salts and hydroxide base, are the most preferred.

The amine to be used in the catalyst include the aliphatic, cycloaliphatic, heterocyclic and aromatic mono and polyamines, such as, for example, triethylamine, tributylamine, laurylamine, benzylamine, dodecylamine, cyclohexylamine, trioctylamine, morpholine, aniline, naphthylamine, dimethylcyclohexylamine, ethylene diamine, N,N,N',N'-tetramethylethylenediamine, N,N,N',N'-tetraethylethylene diamine, piperazine, N-methylpiperazine, N-ethylpiperazine, 2-methyl-N-methylpiperazine, 2,2'-dipyridiyl, purine, 2-aminopyridine, 2-(dimethylamino)pyridine, 1,10-phenanthroline, methyl-substituted 1,10-phenanthroline, piperidine, 2-methylpiperidine, pyridine, ethanolamine, diethanolamine, N,N-dimethylglycine, iminodiacetic acid, N-methyliminodiacetic acid, 2-hydroxypyridine, picolinic acid, methyl-substituted picolinic acid, 2,5-dicarboxypiperazine, ethylenediaminetetraacetic acid, 2,6-dicarboxypiperidine, cyclohexane-1,2-diamine-N,N,N',N'-tetraacetic acid, N-methylpyridine, N-methylpyrrolidine.

Preferred amines to be used in the process of the invention include the aliphatic, cycloaliphatic, heterocyclic and aromatic mono- and poly- primary, secondary and tertiary amines containing up to 20 carbon atoms, and still more preferably the heterocyclic amines containing up to 12 carbon atoms.

The quantity of the ruthenium powder and the cobalt-containing compound to be used in the process of the invention may vary over a wide range. The process is conducted in the presence of a catalytically effective amount of the active ruthenium powder and the active cobalt-containing compound which gives the desired product in a reasonable yield. The reaction proceeds when employing as little as about $1 \times 10^{-6}$ together with as little as about $1 \times 10^{-6}$ weight percent of the cobalt-containing compound, or even lesser amounts, based on the total weight of the reaction mixture. The upper concentration is dictated by a variety of factors including catalyst cost, partial pressures of carbon monoxide, operating temperature, etc. An amount of the ruthenium powder of from about $1 \times 10^{-5}$ to about 5 weight percent in conjunction with a cobalt-containing compound concentration of from about $1 \times 10^{-5}$ to about 5 weight percent, based on the total weight of the reaction mixture is generally desirable in the practice of this invention. The preferred ruthenium to cobalt atomic ratios are from about 10:1 to 1:10.

Generally, in the catalyst system used in the process of the invention, the molar ratio of the ruthenium powder to the quaternary onium salt or base will range from about 1:0.1 to about 1:100 or more, and preferably will be from about 1:1 to about 1:20.

The amount of the amine promoter added to the reaction mixture may vary over a wide range. In general, the amount of the amine will vary from about 0.1 to 15 moles per mole of the ruthenium powder, and still more preferably from about 0.1 to 5 moles per mole of the ruthenium powder.

Particularly superior results are obtained when the above-noted four components of the catalyst system are combined in a molar basis as follows: ruthenium powder 0.1 to 4 moles, cobalt-containing compound 0.1 to 8 moles, the amine 0.1 to 10 moles and the quaternary onium salt or base 0.4 to 60 moles, and still more preferably when the components are combined in the following molar ratios; ruthenium powder 1 to 4 moles, cobalt-containing compound 2 to 4 moles, the amine 0.1 to 5 moles and the quaternary onium base or salt 10 to 50 moles.

Solvents may be and sometimes preferably are employed in the process of the invention. Suitable solvents for the process include the oxygenated hydrocarbons, e.g. compounds possessing only carbon, hydrogen and oxygen and one in which the oxygen atom present is in an ether, ester, ketone carbonyl or hydroxyl group or groups. Generally, the oxygenated hydrocarbon will contain from about 3 to 12 carbon atoms and preferably a maximum of three oxygen atoms. The solvent must be substantially inert under the reaction conditions, must be relatively non-polar and preferably must be one which has a normal boiling point of at least 65° C. at atmospheric pressure and still more preferably the solvent will have a boiling point greater than that of the ester and other products of the reaction so that recovery of the solvent by distillation is facilitated.

Preferred ester type solvents are the aliphatic, cycloaliphatic and aromatic carboxylic acid esters as exemplified by methyl benzoate, isopropyl benzoate, butyl cyclohexanoate, as well as dimethyl adipate. Useful alcohol-type solvents include the monohydric alcohols as cyclohexanol and 2-octanol, etc. Suitable ketone-type solvents include, for example, cyclic ketones, such as cyclohexanone, 2-methylcyclohexanone, as well as acyclic ketones, such as 2-pentanone, butanone, acetophenone, etc. Ethers which may be utilized as solvents include cyclic, acyclic, and heterocyclic materials. Preferred ethers are the heterocyclic ethers as illustrated by 1,4-dioxane and 1,3-dioxane. Other suitable ethers include isopropyl dibutyl ether, diethylene glycol dibutyl ether, diphenyl ether, dibutyl ether, heptyl phenyl ether, anisole, tetrahydrofurane, etc. The most useful solvents of all of the above groups include the ethers, as represented by the polycyclic heterocyclic ethers such as diphenyl ether and 1,4-dioxane, etc.

The amount of the solvent employed may vary over a wide range. In general, it is desirable to use sufficient solvent to fluidize the catalyst system.

The relative amounts of carbon monoxide and hydrogen which may be initially present in the syngas mixture can be varied widely. In general, the mole ratio of CO to $H_2$ is in the range from about 20:1 to 1:20, preferably from about 5:1 to 1:5. Particularly in continuous operations, but also in batch experiments, the carbon monoxide-hydrogen gaseous mixture may also be used in conjunction with up to 50% by volume of one or more other gases. These other gases may include one or more inert gases such as nitrogen, argon, neon and the like, or they may include gases that may or may not undergo reaction under CO hydrogenation conditions, such as methane, ethane, propane, and the like, ethers, such as dimethyl ether and diethyl ether.

The temperature used in the process of the invention may vary over a considerable range. Preferred temperatures range from about 100° C. to about 350° C. The exact temperature selected will depend upon experimental factors, such as the pressure, the concentration and choice of the particular catalyst and cocatalyst selected, etc. Particularly preferred temperatures range from about 150° C. to about 250° C.

Superatmospheric pressures of say at least 500 psi or greater lead to substantial yields of the desired acetaldehyde. In general, pressures varying from about 1000 psi to about 7500 psi give good results and are generally preferred. The pressures referred to herein represent the total pressure generated by all the reactants, although they are substantially due to the carbon monoxide and hydrogen reactants.

The desired product of the reaction, acetaldehyde, will be formed in significant quantities generally varying up to about 56% selectivities. Also formed will be minor by-products including ethanol, methyl and ethyl acetate, and other lower oxygenated products. The acetaldehyde and the by-products can be recovered from the reaction mixture by conventional means, e.g. fractional distillation in vacuo.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired acetaldehyde product, and said material may be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures; viz, gas-liquid phase chromatography (glc), infrared (ir) mass spectrometry, nuclear magnetic resonance (nmr) and elemental analyses, or a combination of these techniques. Analyses have, for the most part, been by parts by weight; all temperatures are in degree centigrade and all pressures in pounds per square inch (psi).

To illustrate the process of the invention, the following examples are given. It is to be understood, however, that the examples are given in the way of illustration and are not to be regarded as limiting the invention in any way.

EXAMPLE I

This example illustrates the improved results obtained by the use of the new catalyst compositions in the preparation of acetaldehyde.

A glass linear was charged with 0.050 g (0.5 mmole) of ruthenium powder, 0.34 g (1.0 mmole) of dicobalt octacarbonyl, 3.40 g (10.0 mmoles) of tetra-n-butylphosphonium bromide, 0.17 g (2.0 mmoles) of N-methylpyrrolidine, 6.4 g of methanol and 20 g. of p-dioxane. The glass liner was placed in a stainless steel reactor, the reactor was purged of air and pressured to 2000 psi with a mixture of carbon monoxide and hydrogen (1:2 molar) and then heated to 202° C. while it was agitated by rocking. The pressure was brought up and maintained at 6500 psi.

The reaction was terminated after 18 hours and the reactor was cooled to room temperature (final pressure 4600 psi). An off-gas sample was collected and excess gas was vented after which 33.0 g of reddish product was collected.

Analysis of the liquid product was by glc; product selectivities were estimated as follows:

56% by weight acetaldehyde
13% by weight ethanol
12% by weight methyl acetate
5% by weight ethyl acetate

EXAMPLE I

Comparative Tests

The following experiment demonstrates the improved selectivity obtained by using the catalysts of the present invention over the results obtained by using catalysts which contain only three components and is free of the amine promoter.

The above procedure was repeated with the exception that the catalyst system comprised 0.5 mmole ruthenium powder, 5 mmole tetra-n-butylphosphonium bromide and 1 mmole of dicobalt octacarbonyl. 6.4 grams of methanol and 20 grams of p-dioxane were added to the reaction mixture along with the above-noted catalyst. Synthesis gas was added in a 2:1 ($H_2$:CO) molar mix, the operating temperature was 2000° C. and the pressure range from 5800 to 6250 psi for a period of 18 hours. The liquid product showed a weight gain of 2.3 grams and a product selectivity of:

38% by weight acetaldehyde
23% by weight ethanol
5% by weight methyl acetate
7% by weight ethyl acetate It should be noted that the selectivity to acetaldehyde of 56% obtained by using the process of the invention which contains the amine promoter in the catalyst system is higher than the 38% selectivity obtained by use of the above process which contained no amine promoter in the catalyst system.

EXAMPLES II TO VIII

The synthesis procedure of Example I was repeated with the exception that the nature of the amine promoter was changed and the proportions of the catalyst composition. The results are summarized in Table I.

It may be noted that a variety of amine promoter structures are effective in improving both the level of methane conversion and the selectivity to acetaldehyde. Particularly effective are heterocyclic amines, such as 3-hydroxypyridine.

TABLE NO. I

| EXAMPLE | Ru/ n-bu$_4$PBr/ Co$_2$(CO)$_8$ Catalyst (mmole used) | Promoter (mmole used) | Reaction (a) (b) Conditions | Methanol Conversions (%) | H$_2$O % (K.F.) | Product Selectivity (wt %) | | | | | Wt. gain (g) |
|---|---|---|---|---|---|---|---|---|---|---|---|
| | | | | | | CH$_3$CHO | C$_2$H$_5$OH | CH$_3$OAc | EtO Ac | HO Ac | |
| II | (0.5:10:1) | 3-hydroxy-pyridine (1 mm) | 6300 psi 200° C. 18 hrs | 92 | 8.53 | 51 | 10 | 10 | 9 | 0 | 2.7 |
| III | (0.5:10:1) | 3-hydroxy-pyridine (3 mm) | 6300 psi 200° C. 18 hrs | 69 | 5.66 | 48 | 26 | 13 | 6 | 0 | 2.5 |
| IV | (0.5:10:1) | 2-hydroxy-pyridine (3 mm) | 6250–4680 psi 200° C. 18 hrs | 90 | 8.79 | 41 | 18 | 9 | 10 | 0 | 3.2 |
| V | (0.5:10:2) | N—methyl pyrrolidine (2 mm) | 6500–5300 psi 200° C. 18 hrs | 77 | 7.17 | 33 | 24 | 13 | 16 | 0 | 1.4 |
| VI | (0.5:10:1) | N—methyl pyrrolidone (1 mm) N—methyl-pyrrlidine (2 mm) + | 6300–5000 psi 200° C. 18 hrs | 88 | 7.79 | 44 | 10 | 12 | 9 | 0 | 1.9 |
| VII | (0.5:10:1) | N—methyl-pyrrolidone (2 mm) | 6500–6375 psi 200° C. 18 hrs | 33 | 23 | 42 | 2 | 12 | 22 | 0 | — |
| VIII | (0.5:10:0.5) | 3-hydroxy-pyridine (1 mm) | 6100 psi 200° C. 4 hrs | 54 | 4.1 | 35 | 0 | 18 | 46 | 0 | — |

(a) CO/H$_2$ = 1:2
(b) methanol (6.3 g) and p-dioxane (20.0 g) were charged

What is claimed is:

1. A process for preparing acetaldehyde from methanol and syngas which comprises contacting a mixture of methanol, carbon monoxide and hydrogen with a catalytic amount of an iodide or iodine-free catalyst composition comprising ruthenium powder, a cobalt-containing compound, from the group consisting of cobalt oxides, cobalt salts, cobalt carbonyl compounds and derivatives thereof, an amine, and an onium base or salt, and heating the resulting mixture to a temperature of at least 100° C. and a pressure of at least 500 psi for sufficient time to produce the acetaldehyde.

2. A process as in claim 1 wherein the cobalt-containing compound is a member of the group consisting of cobalt carbonyls and derivatives thereof obtained by reacting the carbonyls with a group V donor ligand, cobalt carbonyl hydrides, cobalt carbonyl chlorides and bromides, cobalt chlorides and bromides and cobalt salts of organic carboxylic acids.

3. A process as in claim 1 wherein the cobalt-containing compound is a cobalt compound having at least one cobalt atom linked to at least three separate carbon atoms.

4. A process as in claim 1 wherein the quaternary onium salt or base is a quaternary phosphonium salt or base.

5. A process as in claim 1 wherein the quaternary onium salt or base is a tetrahydrocarbylphosphonium salt having from 1 to 10 carbon atoms in each of the hydrocarbyl groups.

6. A process as in claim 5 wherein the salt is selected from the group consisting of tetrahydrocarbylphosphonium bromides, chlorides, and chromates.

7. A process as in claim 1 wherein the amine is selected from the group consisting of aliphatic amines, cycloaliphatic amines and heterocyclicamines and aromatic amines containing up to 16 carbon atoms.

8. A process as in claim 1 wherein the amine is a heterocyclic amine containing up to 10 carbon atoms.

9. A process as in claim 1 wherein the amine is a N-alkyl pyrrolidine.

10. A process as in claim 1 wherein the catalyst components are utilized in the following molar ratios: ruthenium powder 0.1 to 4 moles; cobalt-containing compound 0.1 to 8 moles; amine 0.1 to 6 moles; quaternary onium salt or base 0.4 to 60 moles.

11. A process as in claim 1 wherein the carbon monoxide and hydrogen are employed in a molar ratio varying from 5:1 to 1:5.

12. A process as in claim 1 wherein the reaction in conducted at a temperature between 150° C. and 350° C.

13. A process as in claim 1 wherein the reaction is conducted at a pressure between 1000 psi and 7500 psi.

14. A process for preparing acetaldehyde from methanol and syngas which comprises contacting a mixture of methanol, carbon monoxide and hydrogen with a catalytic amount of iodide or iodine-free catalyst composition comprising ruthenium powder, a cobalt carbonyl, a heterocyclic amine and a quaternary tetrahydrocarbyl phosphonium chloride or bromide, and heating the resulting mixture to a temperature between 150° C. and 350° C. and a pressure between 1000 psi and 7500 psi for sufficient time to produce the desired acetaldehyde, and then recovering the same from the reaction mixture.

15. A process as in claim 1 wherein a solvent is included in the reaction mixture.

16. A process as in claim 15 wherein the solvent is a heterocyclic ether.

17. A process as in claim 15 wherein the solvent is dioxane.

18. A process as in claim 1 wherein the cobalt-containing compound is dicobalt octacarbonyl.

19. A process as in claim 1 wherein the onium-containing compound is n-heptyltriphenylphosphonium bromide.

20. A process as in claim 1 wherein the amine is 3-hydroxypyridine.

21. A process as in claim 1 wherein the amine is N-methyl pyrrolidine.

22. A process as in claim 1 wherein the amine is N-methyl pyrrolidone.

23. A process as in claim 1 wherein the amine is 2-hydroxypyridine.

* * * * *